United States Patent [19]

Bradford

[11] Patent Number: Plant 5,654

[45] Date of Patent: Feb. 4, 1986

[54] NECTARINE TREE (SUMMER DIAMOND)

[76] Inventor: Norman G. Bradford, 11875 Savana Rd., Le Grand, Calif. 95333

[21] Appl. No.: 622,088

[22] Filed: Jun. 18, 1984

[51] Int. Cl.[4] ..... A01H 5/03

[52] U.S. Cl. ..... Plt./41

[58] Field of Search ..... Plt./41

*Primary Examiner*—Robert E. Bagwill

[57] ABSTRACT

The instant variety, having the cultivar name Summer Diamond, is a new and distinct variety of nectarine tree broadly characterized by a medium size, vigorous, hardy, very productive and regular bearing tree, the fruit of which ripens about the same time as the Fantasia (unpatented) nectarine under the ecological conditions described. The fruit is freestone, very firm and crisp, and has a uniformy bright red skin color. It is also globose to slightly oblong in shape, of better eating quality, and has a sweet kernel.

1 Drawing Figure

BACKGROUND OF THE VARIETY

The instant variety of nectarine tree ripens at the same time as the Fantasia (believed to be an unpatented variety), but is distinguished therefrom and an improvement thereon in being much firmer and having a more attractive globose to slightly oblong form and a uniformly bright red skin color, and is of better eating quality. It is further distinguished by having a sweet kernel.

The instant variety is also similar to its parent plant Red Diamond (U.S. Plant Pat. No. 3,165) in having a similar shape, color and firmness. It differs, however, in the fact that it ripens around 23 days later than Red Diamond, thereby giving the grower a much needed firm freestone nectarine ripening in a later season, which is important for long distance shipping. I have compared the variety to the Fantasia because of its similar ripening time.

The instant variety was propagated by me at Bradford Farms in Merced County (San Joaquin Valley), Calif., as the result of open pollination of a Red Diamond nectarine. I asexually reproduced the resulting plant by budding and grafting, and such reproduction of plant and fruit characteristics were true to the original plant in all respects.

DRAWING

The accompanying photograph shows the characteristics of the whole fruit in skin color and form, a characteristic fruit divided on its suture plane showing the flesh and stone cavity, and a characteristic stone, and leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the stage of eating ripe in the 1983 growing season. All color plate identifications are by reference to Dictionary of Color 1950 (2d ed) by Maerz and Paul.

Tree:

*General.*—Hardy, vigorous, spreading and dense, of medium size and vase shaped. Very productive and regular bearing.

Trunk: Medium size, shaggy bark resembling Dark Beaver 15 A-9, numerous lenticels ⅛" in length.

Branches: Medium size, medium shaggy; second year and older growth resembling Burnt Umber 15 A-12 in color, newer growth is reddish brown on dorsal side, lighter (15 C-7) on ventral side. Numerous medium size, tan lenticels ⅛" to 1/16" long.

Leaves:

*Size.*—Medium; 5½" in length, 1½" in width.

*Base.*—Acute.

*Apex.*—Acuminate.

*Margin.*—Crenate.

*Veins.*—Pinnately net veined.

*Petiole.*—Medium — Length ½".

*Glands.*—Two to four oppositely disposed, medium size, reniform, green; positioned usually two on the petiole and sometimes on base of blade.

*Stipules.*—Numerous, ⅛" long.

*Leaf color.*—Dorsal side resembles Cedar Green 22 L-5, ventral side resembles 22 L-1.

Flower, buds:

*Buds.*—Hardy, medium length and circumference; obtuse, plump, free and pubescent.

*Flowers.*—Bloom medium season compared with other varieties. Small, pink.

Fruit:

*Maturity when described.*—Full ripe, on Aug. 2, 1983.

*Size.*—Uniform, medium size; axial diameter 2⅝", transverse in suture plane, 2⅜".

*Form.*—Uniform, symmetrical; globose to slightly oblong. Slightly obovate in longitudinal section, circular transverse through diameter.

*Suture.*—An inconspicuous shallow line extending from base but discontinuing at apex, slight depression beyond pistil point.

*Ventral surface.*—Rounded, lipped only slightly with equal lips.

*Cavity.*—Abrupt and circular, with suture showing on one side. Depth ½", breadth, ½". Base: Truncate. Apex: Short, depressed. Pistil Point: Apical but almost nonexistant. Stem: ⅜" in length, 3/16" in width. Skin: In general, of medium thickness, tender texture; tenacious to flesh. Only slight tendency to crack.

*Skin color.*—Resembles Autumn Glory 5 K-12 over Golden Glow 9 L-6.

*Flesh.*—Juice: Moderate. Texture; Very firm, crisp. Fibres: Abundant, fine and tender. Ripens evenly. Flavor: Subacid. Aroma: Wanting. Eating Quality: Very good to best. Color: Resembles Sunshine 10 K-7.

Stone:

*Type.*—Freestone.

*Form.*—Oblong.

*Base.*—Acute.

*Hilum.*—Narrow.

*Apex.*—Acute, flattened, equal sides.

*Surface.*—Irregularly furrowed and pitted throughout.

*Ridges.*—Rounded.

*Color.*—Resembles 15 A-10.

*Thickness to pit wall.*—3/16".

*Tendency to split.*—Only slight.

*Kernel.*—Oval, sweet, viable. Size, width ½", length, ¾"; scant amygdalin.

Use: Market, long distance shipping, Excellent keeping quality, excellent shipping quality.

I claim:

1. A new and distinct variety of freestone nectarine tree, substantially as illustrated and described, which most nearly resembles the Fantasia (unpatented) variety but is distinguished therefrom and an improvement thereon by bearing fruit which ripens at the same time but is much firmer and remains firm for a longer time on the tree, has a more attractive, globose to slightly oblong shape and a uniformly bright red skin color.

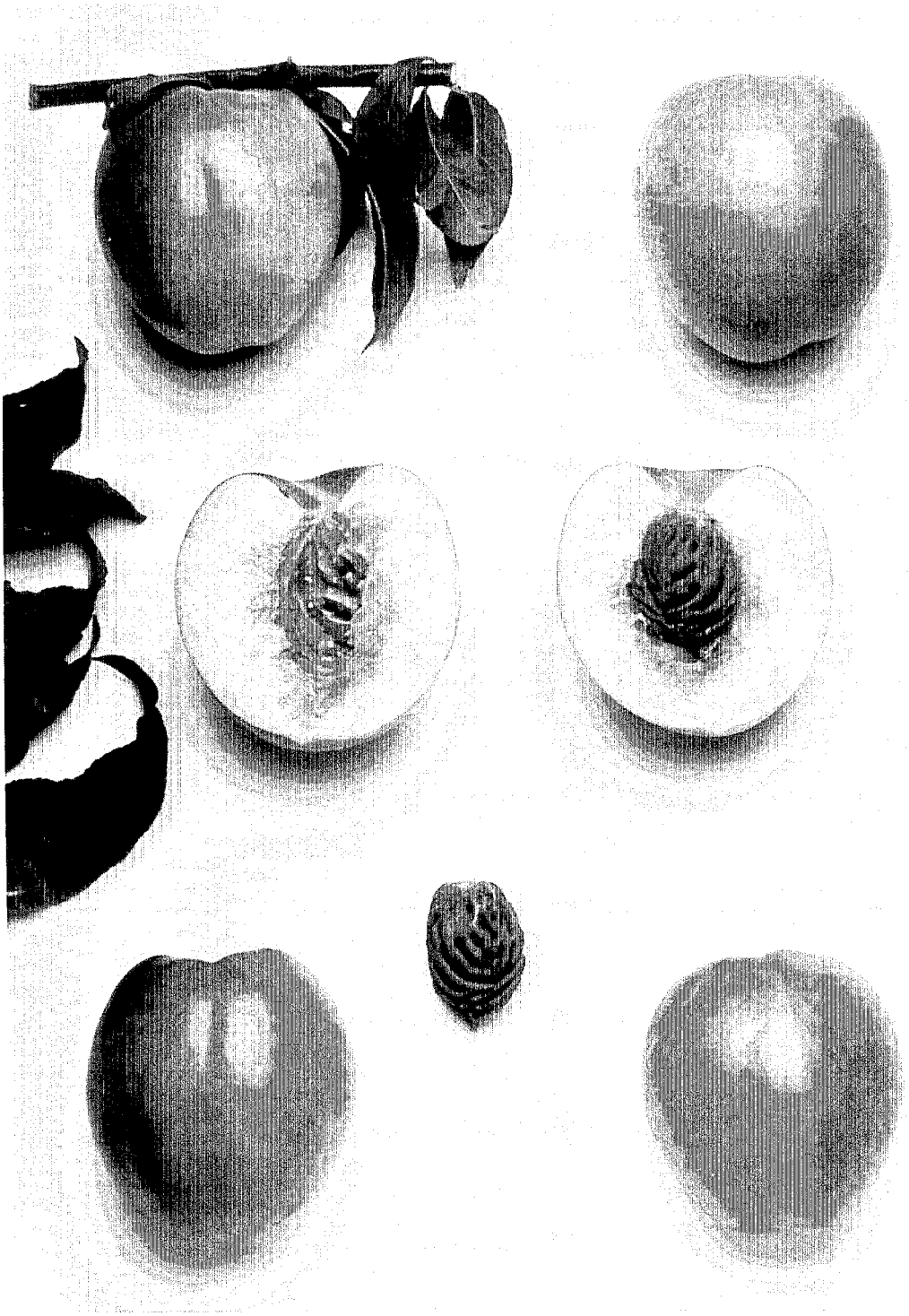

* * * * *